United States Patent [19]

Leistner et al.

[11] 4,052,427
[45] Oct. 4, 1977

[54] PROCESS FOR THE PREPARATION OF DIALKYLTIN DIHALIDES

[75] Inventors: William E. Leistner, Atlanta Beach, N.Y.; Gerald H. Spiegelman, Wayne; Louis J. Hover, Oak Ridge, both of N.J.

[73] Assignee: Witco Chemical Corporation, New York, N.Y.

[21] Appl. No.: 698,451

[22] Filed: June 21, 1976

[51] Int. Cl.² .................................... C07F 7/22
[52] U.S. Cl. ...................................... 260/429.7
[58] Field of Search .......................... 260/429.7

[56] References Cited

U.S. PATENT DOCUMENTS

| 3,415,857 | 12/1968 | Hoye | 260/429.7 |
| 3,475,472 | 10/1969 | Suzuki et al. | 260/429.7 |
| 3,475,473 | 10/1969 | Tahara et al. | 260/429.7 |
| 3,519,667 | 7/1970 | Molt et al. | 260/429.7 |
| 3,792,059 | 2/1974 | Hechenbleikner | 260/429.7 |

OTHER PUBLICATIONS

Chemical Abstracts, V68, 87373z (1968).
Chemical Abstracts, V57, 2239i (1962).
Kuvila et al., J. Org. Chem. V33, 1119–1122 (1968).

*Primary Examiner*—Helen M. S. Sneed
*Attorney, Agent, or Firm*—Albert L. Gazzola; Morton Friedman

[57] ABSTRACT

The preparation of dialkyltin dihalides and mixed dialkyltin dihalides, by refluxing a dimethyltin dihalide with a higher alkyl-halide in the presence of a phosphonium iodide catalyst, useful as intermediates for PVC stabilizers.

11 Claims, No Drawings

PROCESS FOR THE PREPARATION OF DIALKYLTIN DIHALIDES

The present invention relates to the preparation of dialkyltin dihalides from a dimethyltin dihalide using a phosphonium iodide catalyst.

In U.S. Pat. No. 3,519,665, a process is described for the preparation of dialkyltin dichlorides by reacting tin metal with an alkyl chloride in the presence of a phosphonium iodide catalyst and separating the dialkyltin dichloride from other tin containing reaction products and catalyst.

In U.S. Pat. No. 3,415,857 there is described another such process for the production of organotin halides by reacting metallic tin with an aliphatic halide, in the presence of an organic 'onium catalyst.

In the foregoing processes, wherein reaction with tin is involved, considerable dehydrohalogenation occurs when the alkyl groups are not methyl.

Dialkyltin dichlorides can also be prepared by disproportionation of tetra-alkyl tin with tin tetrachloride by known processes. The processes are complicated and require the consuming of another metal, such as magnesium, aluminum, and sodium.

By the present invention there is provided a process for the preparation of certain dialkyltin dihalides, and more particularly dialkyltin dichlorides wherein one alkyl group is methyl and the other, a $C_2$-$C_{20}$ alkyl, or both alkyl groups may be $C_2$-$C_{20}$ alkyls, and mixtures thereof, by heating dimethyltin dichloride with the desired alkyl chloride, for instance, in the presence of a phosphonium iodide catalyst. The reaction does not proceed without the phosphonium iodide.

The starting dimethyltin dichloride may be conveniently prepared by the direct reaction of the methyl chloride and tin metal as known in the art.

Otherwise stated the present invention comprises a process for the preparation of dialkyltin dihalides of the formula:

R-R'-SnX$_2$ wherein R is R' or methyl, and R' is a $C_2$-$C_{20}$ alkyl, and mixtures comprising (a) heating Me$_2$SnX$_2$ and R'X, wherein X is chlorine bromine or iodine, in the presence of a phosphonium iodide catalyst; and (b) recovering by known methods the dialkyl tin dihalide product.

The alkyl-halide employed in the instant invention, as shown above, may be alkyl chloride, bromide, or iodide. The alkyl group may be straight or branched chain alkyl, or cyclic alkyl, and may be an aralkyl group, and is preferably a primary halide. The alkylhalide is preferably alkyl-chloride and may be, for example, ethyl, butyl, isopropyl, hexyl, cyclohexyl, or octyl chloride and preferably the alkyl contains 4 to 12 carbon atoms. Aralkyl-halides such as chloropropyl benzene and phenyl stearyl chloride may also be employed in the present process.

As the catalyst there is employed a phosphonium iodide. It is generally preferred to employ the iodide since when employing phosphonium bromides or chlorides, for instance, the reaction goes much more slowly. Examples of suitable phosphonium iodides are tetramethyl phosphonium iodide, tetraethyl phosphonium iodide, tetrapropyl phosphonium iodide, tetrabutyl phosphonium iodide, tetraisopropyl phosphonium iodide, tetraoctyl phosphonium iodide, tetradodecyl phosphonium iodide, tetraoctadecyl phosphonium iodide, tetraphenyl phosphonium iodide, tetrabenzyl phosphonium iodide, octyl triphenyl phosphonium iodide, methyl triphenyl phosphonium iodide, dodecyl triphenyl phosphonium iodide, phenyl ethyl tetramethylene phosphonium iodide, tetra p-tolyl phosphonium iodide. The phosphonium iodide is normally used in an amount of 0.1 to 0.6 moles per atom of tin, but the amount is not critical, as known in the art.

Although corresponding quaternary ammonium iodides may also be emloyed in the present reaction, they offer no additional advantage and are not preferred.

The phosphonium iodide need not be preformed but can be formed in situ by adding the appropriate reagents. Thus, the phosphonium iodides can be formed in situ for example by adding an alkyl iodide to a secondary or tertiary phosphine. Thus, if tributyl phosphine and methyl iodide are added to the reaction mixture there is formed methyl tributyl phosphonium iodide. Similarly from tributyl phosphine and ethyl iodide there is formed ethyl tributyl phosphonium iodide, from trioctyl phosphine and octyl iodide there is formed tetraoctyl phosphonium iodide.

Since the present reaction may involve intermediate reaction with the catalyst, the organic groups present in the catalyst are preferably the same as those of the organic halide of the reaction to insure a uniformity of product, when this is desired.

The present process is generally carried out under reflux conditions at temperatures of from about 125° to about 225° C and preferably from about 150° to about 200° C. The reaction may be carried out for from about 1 to 50 hours at the aforesaid temperatures and preferably between 5 and 25 hours.

Without wishing to be bound by any theory or mechanism it is believed that the reaction of the subject invention proceeds in a stepwise manner as shown in equations (I) and (II) below:

$$Me_2SnCl_2 + R'Cl \xrightarrow{cat.} Me(R')SnCl_2 + MeCl \quad (I)$$

$$Me(R')SnCl_2 + R'Cl \xrightarrow{cat.} R'_2SnCl_2 + MeCl \quad (II)$$

wherein Me is methyl and R' is a $C_2$-$C_{20}$ alkyl group and preferably $C_4$-$C_{12}$.

Confirmation of the alkyl exchange is obtained by infrared analysis of the MeCl gas evolved during the reaction.

It is also within the comtemplation of this invention that the process start with the preparation of Me$_2$SnCl$_2$ by the direct reaction of Sn and MeCl, and wherein the MeCl formed in reactions (I) and (II) is recycled to the initial reaction to form the Me$_2$SnCl$_2$.

In the reactions (I) and (II) it is desirable that the molar ratio of R'Cl to Me$_2$SnCl$_2$ be in the range of 1:1 to 3:1. When a predominantly mixed dialkyl tin dichloride is desired, i.e. in which one alkyl is methyl, only one mole, or a little excess alkyl chloride is employed. When a predominantly $C_4$-$C_{20}$ dialkyl tin dichloride is desired, a little excess of two moles of alkyl chloride is employed. Excess alkyl-halide of considerably more than two moles, i.e. three, four, or more moles, may be employed, but offers no real advantage in this reaction.

It is to be noted that reacting dimethyltin dichloride, for instance, with two or more moles, of alkyl-halide, as the case may be, because of competitive reactions, as known in the art, the products are generally mixtures of dialkyltin dihalides, i.e. when reacting more than two moles of octyl chloride with dimethyltin dichloride, the product is predominantly dioctyltin dichloride, but contains some methyl octyltin dichloride and some starting material. Similarly, when reacting a little excess of one mole of alkyl chloride such as butyl chloride with dimethyltin dichloride, the product is predominantly methylbutyltin dichloride, but contains some dibutyltin dichloride and some starting material. These mixtures are useful as intermediates for polyvinyl chloride stabilizers, for instance, as is well known in the art. They need not be pure products for this use. Methylbutyl or methyloctyltin dichloride, for instance, are excellent for this purpose.

If a pure dialkyltin dichloride is desired, it may be separated from he other components in any convenient manner, e.g. by fractional distillation or solvent crystallization, as known in the art.

The following examples are further illustrative of the present invention.

EXAMPLE I

Apparatus was set up comprising a 4-neck, 500 ml round bottom flash fitted with stirrer, thermometer, and reflux condenser. A dry ice trap and drying tube were attached to the system through the top of the condenser. Reactants were 58g (0.26 mole) $Me_2SnCl_2$ and 93g (0.61 mole) octyl chloride, and 52g (0.1 mole) octyl$_4$PI were placed in the reaction vessel. The pot temperature was raised to 180° C, with stirring. The mixture was maintained at reflux, and samples were withdrawn periodically for analysis. When the evolution of MeCl had ceased, the product was then distilled under atmospheric pressure to remove octene and excess octyl chloride.

The analysis of the product is conducted on an F&M Model No. 500 GLC equipped with a 5 inch × ⅛ inch 20% SE-30 on Chromosorb W column. Instrument settings are: injection port, 325° C; Detector, 310° C, and 150 MA; carrier gas, Helium, 50 ml/min. Programming from 125 to 300° C at 30°/min. for octyl, and from 125° to 250° C at 11°/min. for butyl, for instance, give good resolution. Confirmation of dioctyltin dichloride and octyl methyltin dichloride are made by comparison with known samples.

Positive identifications of methyloctyltin dichloride and dioctyltin is obtained by comparison of gas chromtographic retention times, infrared, and nmr spectra with the data obtained on authentic samples. For this purpose, methyloctyltin dichloride was prepared by the method of H. G. Kuvila et al., Journal Organic Chem., 33, 1119 (1968), using the reaction of trioctyltin chloride with methyltin trichloride. The properties of the product agreed with those previously reported, Chemical Abstracts, 68, 8737z (1968).

EXAMPLE II

Methylbutyltin dichloride is prepared by gradually adding excess of one mole (10% excess of butyl chloride to a stirred solution of butyl$_4$PI in dimethyltin dichloride at 160°–180° C under reflux as in Example I. The product is distilled at atmospheric pressure to remove butene and excess butyl chloride.

While the invention has been described with particular reference to specific embodiments, it is to be understood that it is not to be limited thereto.

What is claimed is:

1. A process for the preparation of dialkyltin dihalides of the formula:

R R'-SnX$_2$ 

wherein R equals methyl or R'; R' equals $C_2$-$C_{20}$ alkyl; and X equals halogen; comprising;
 a. refluxing $Me_2SnX_2$ and R'X in a molar ratio of about 1:1 to 1:3 in the presence of a phosphonium iodide catalyst at about 150°–200° C for from 1 to 50 hours and;
 b. recovering the dialkyltin dihalide product having one or more methyl group of the $Me_2SnX_2$ replaced by R'.

2. The process of claim 1, wherein X is chlorine.

3. The process of claim 1, wherein the catalyst is a tetra-alkyl phosphonium iodide.

4. The process of claim 1, wherein R' is from $C_4$-$C_{12}$.

5. The process of claim 1, wherein R'X is octyl chloride and the catalyst is tetraoctyl phosphonium iodide.

6. The process of claim 1, wherein the reactants are refluxed for about 5 to about 25 hours.

7. A process for the preparation of a dialkyltin dichloride comprising,
 a. reacting methyl chloride with tin to form dimethyltin dichloride;
 b. refluxing the dimethyltin dichloride with a $C_2$-$C_{20}$ alkyl chloride in the presence of a phosphonium iodide catalyst at about 150°–200° C, and;
 c. recovering the dialkyltin dichloride from the reaction products.

8. The process of claim 7, wherein the reactants (b) are heated for about 5 to 25 hours.

9. The process of claim 7, wherein the alkyl chloride is $C_4$-$C_{12}$ alkyl.

10. The process of claim 7, wherein the recovered methyl chloride is recycled to step (a).

11. The process of claim 7, wherein said alkyl chloride is butyl chloride and said catalyst is tetrabutyl phosphonium iodide.

* * * * *